(12) United States Patent
Ozcan et al.

(10) Patent No.: US 8,219,350 B2
(45) Date of Patent: *Jul. 10, 2012

(54) APPARATUS FOR MEASURING A FREQUENCY-DOMAIN OPTICAL COHERENCE TOMOGRAPHY POWER SPECTRUM FROM A SAMPLE

(75) Inventors: Aydogan Ozcan, Boston, MA (US); Michel J. F. Digonnet, Palo Alto, CA (US); Gordon S. Kino, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/224,555

(22) Filed: Sep. 2, 2011

(65) Prior Publication Data

US 2011/0317167 A1    Dec. 29, 2011

Related U.S. Application Data

(60) Continuation of application No. 12/372,225, filed on Feb. 17, 2009, now Pat. No. 8,032,322, which is a division of application No. 11/384,170, filed on Mar. 17, 2006, now Pat. No. 7,493,227.

(60) Provisional application No. 60/662,652, filed on Mar. 17, 2005.

(51) Int. Cl.
*G06F 17/14*    (2006.01)
*G01N 21/00*    (2006.01)

(52) U.S. Cl. ............................ 702/127; 702/77; 356/497

(58) Field of Classification Search .................. 702/127, 702/77, 76, 159

See application file for complete search history.

(56) References Cited

U.S. PATENT DOCUMENTS

| 4,627,731 A | 12/1986 | Waters et al. |
| 5,530,544 A | 6/1996 | Trebino et al. |
| 5,682,262 A | 10/1997 | Wefers et al. |
| 5,909,659 A | 6/1999 | Fujita |

(Continued)

FOREIGN PATENT DOCUMENTS

JP    05-52740    3/1993

(Continued)

OTHER PUBLICATIONS

Choma, Michael A., et al., *Sensitivity advantage of swept source and Fourier domain optical coherence tomography*, Optics Express, vol. 11, 2003, pp. 2183-2189.

(Continued)

*Primary Examiner* — Hal Wachsman
(74) *Attorney, Agent, or Firm* — Knobbe, Martens, Olson & Bear LLP

(57) ABSTRACT

An apparatus is provided for measuring a frequency-domain optical coherence tomography power spectrum from a sample. The apparatus includes a partially reflective element configured to be optically coupled to a light source and to the sample. A first portion of light from the light source is configured to be reflected by the partially reflective element. A second portion of light from the light source is configured to propagate through the partially reflective element, to impinge the sample, and to reflect from the sample. The apparatus is configured to receive the first and second portions of light and to measure the frequency-domain optical coherence tomography power spectrum in response to the first portion of light and the second portion of light.

20 Claims, 10 Drawing Sheets

U.S. PATENT DOCUMENTS

| | | | |
|---|---|---|---|
| 5,994,690 | A | 11/1999 | Kulkarni et al. |
| 6,002,480 | A | 12/1999 | Izatt et al. |
| 6,219,142 | B1 | 4/2001 | Kane |
| 6,456,380 | B1 | 9/2002 | Naganuma |
| 6,539,148 | B1* | 3/2003 | Kim et al. ............... 385/27 |
| 6,657,727 | B1 | 12/2003 | Izatt et al. |
| 7,019,838 | B2 | 3/2006 | Izatt et al. |
| 7,130,052 | B1 | 10/2006 | Kane |
| 7,359,062 | B2 | 4/2008 | Chen et al. |
| 7,369,953 | B2 | 5/2008 | Ozcan et al. |
| 7,643,952 | B2 | 1/2010 | Ozcan et al. |
| 7,733,497 | B2 | 6/2010 | Yun et al. |
| 8,032,322 | B2* | 10/2011 | Ozcan et al. ............. 702/127 |
| 2003/0174335 | A1 | 9/2003 | Sun et al. |
| 2004/0239938 | A1 | 12/2004 | Izatt |
| 2004/0239943 | A1 | 12/2004 | Izatt et al. |
| 2004/0246490 | A1* | 12/2004 | Wang ...................... 356/479 |
| 2006/0055936 | A1* | 3/2006 | Yun et al. ................ 356/479 |
| 2007/0103683 | A1* | 5/2007 | Wang ...................... 356/364 |
| 2008/0031410 | A1* | 2/2008 | Shimizu et al. ........... 378/21 |

FOREIGN PATENT DOCUMENTS

| | | |
|---|---|---|
| JP | 05-264402 | 10/1993 |
| JP | 10-10047 | 1/1998 |

OTHER PUBLICATIONS

European Examination Report re Application No. 06 738 710.0, dated Jan. 20, 2010.

European Examination Report re Application No. 06 738 710.0, dated Aug. 22, 2011.

Fercher, A.F., et al., *Measurement of intraocular distances by backscattering spectral interferometry, Opt. Commun.*, vol. 117, 1995, Abstract, one page.

Fercher, A.F., et al., *Optical Coherence Tomography in Medicine*, from Asakura, T., *International trends in optics and photonics ICO IV*, Springer-Verlag, Berlin Heidelberg, 1999, pp. 359-389.

Fienup, J.R., *Reconstruction of an object from the modulus of its Fourier transform, Opt. Lett.*, vol. 3, 1978, pp. 27-29.

Fujimoto, James G., et al., *Optical biopsy and imaging using optical coherence tomography, Nature Medicine*, vol. 1, 1995, pp. 970-972.

Gerchber, R.W., et al., *Practical algorithm for the determination of phase from image and diffraction plane pictures, Optik*, vol. 35, 1972, Abstract, one page.

Häusler, Gerd, et al., *Coherence radar and spectral radar—New tools for dermatological diagnosis, J. Biomed. Opt.*, vol. 3, 1998, pp. 21-31.

Hayes, Monson H., et al., *Signal reconstruction from phase or magnitude, IEEE Trans. Acoust., Speech, Signal Processing*, vol. 28, 1980, pp. 672-680.

Huang, David, et al., *Optical coherence tomography, Science*, vol. 254, 1991, pp. 1178-1181.

International Search and Written Report re PCT/US2006/009677, dated Oct. 30, 2006.

Leitgeb, R.A., et al., *Performance of Fourier domain vs. time domain optical coherence tomography, Optics Express*, vol. 11, 2003, pp. 889-894.

Leitgeb, R.A., et al., *Ultrahigh resolution Fourier domain optical coherence tomography, Optics Express*, vol. 12, 2004, pp. 2156-2165.

Leitgeb, Rainer A., et al., *Phase-shifting algorithm to achieve high-speed, long-depth-range probing by frequency domain optical coherence tomography, Opt. Lett.*, vol. 28, 2003, pp. 2201-2203.

Office Action for Japanese Patent Application No. 2006-541655 dated May 18, 2010.

Office Action for Japanese Patent Application No. 2006-541655 dated Jan. 18, 2011.

Oppenheim, V. and Schafer, R.W., *Digital Signal Processing*, Prentice Hall, 2002, Chapter 7.

Ozcan, A., et al., *Frequency-domain coherence tomography based on minimum-phase functions, Proc. of SPIE*, vol. 6079, Edward L. Ginzton Laboratory, Stanford University, Stanford, CA, 12 pages, 2006.

Ozcan, A., et al., *Group delay recovery using iterative processing of amplitude of transmission spectra of fibre Bragg Gratings, Electron. Lett.*, vol. 40, No. 18, 2004, two pages.

Ozcan, A. et al., *Inverse Fourier transform technique to determine second-order optical nonlinearity spatial profiles, Applied Physics Letters*, vol. 82, No. 9, Mar. 3, 2003, pp. 1362-1364.

Ozcan, A., et al., *Iterative processing of second-order optical nonlinearity depth profiles, Opt. Express*, vol. 12, 2004, pp. 3367-3376.

Peatross, J., et al., *Temporal decorrelation of short laser pulses, J. Opt. Soc. Am. B*, vol. 15, No. 1, Jan. 1998, pp. 216-222.

Peri, David, *Optical implementation of a phase retrieval algorithm, Applied Optics*, vol. 26, Issue 9, 1987.

Petermann, E. Ingemar, et al., *Characterization of Fiber Bragg Gratings by Use of Optical Coherence-Domain Reflectometry, Journal of Lightwave Technology*, vol. 17, No. 11, Nov. 1999, pp. 2371-2378.

Pureur, D., et al., *Absolute measurement of the second-order nonlinearity profile in poled silica, Optics Letters*, vol. 23, No. 8, Apr. 15, 1998, pp. 588-590.

Quatieri, Thomas F., Jr., et al., *Iterative techniques for minimum phase signal reconstruction from phase or magnitude, IEEE Trans. Acoust., Speech, Signal Processing*, vol. 29, 1981, pp. 1187-1193.

Vakhtin, A.B., et al., *Common-path interferometer for frequency-domain optical coherence tomography, Applied Optics*, vol. 42, No. 34, Dec. 1, 2003, pp. 6953-6958.

Wojtkowski, Maciej, et al., *In vivo human retinal imaging by Fourier domain optical coherence tomography, J. Biomed. Opt.*, vol. 7, 2003, pp. 457-463.

\* cited by examiner

APPARATUS FOR MEASURING A FREQUENCY-DOMAIN OPTICAL COHERENCE TOMOGRAPHY POWER SPECTRUM FROM A SAMPLE

CLAIM OF PRIORITY

This application is a continuation of U.S. patent application Ser. No. 12/372,225, filed Feb. 17, 2009, now U.S. Pat. No. 8,032,322, and incorporated in its entirety by reference herein, which is a divisional of U.S. patent application Ser. No. 11/384,170, filed Mar. 17, 2006, now U.S. Pat. No. 7,493, 227, and incorporated in its entirety by reference herein, and which claims the benefit of U.S. Provisional Application No. 60/662,652, filed Mar. 17, 2005, which is incorporated in its entirety by reference herein.

BACKGROUND OF THE INVENTION

1. Field of the Invention

The present invention relates generally to apparatuses and methods for optical coherence tomography, and more specifically to apparatuses and methods for providing improved optical coherence tomography images.

2. Description of the Related Art

Optical coherence tomography (OCT) is widely used in medicine to image tissues of various part of the body. See, e.g., T. Asakura, "*International trends in optics and photonics ICO IV*," (Springer-Verlag, Berlin Heidelberg, 1999) pp. 359-389; D. Huang, et al. "*Optical coherence tomography,*" *Science*, Vol. 254, pp. 1178-1181 (1991); J. G. Fujimoto, et al. "*Optical biopsy and imaging using optical coherence tomography,*" *Nature Medicine*, Vol. 1, pp. 970-972 (1995); A. F. Fercher, C. K. Hitzenberger, G. Kamp, and S. Y. El-Zaiat, "*Measurement of intraocular distances by backscattering spectral interferometry,*" *Opt. Commun.*, Vol. 117, pp. 43-48 (1995); G. Hausler and M. W. Lindler, "*Coherence radar and spectral radar—New tools for dermatological diagnosis,*" *J. Biomed. Opt.*, Vol. 3, pp. 21-31 (1998); M. Wojtkowski, R. A. Leitgeb, A. Kowalczyk, T. Bajraszewski, and A. F. Fercher, "*In vivo human retinal imaging by Fourier domain optical coherence tomography*", *J. Biomed. Opt.*, Vol. 7, pp. 457-463 (2003); R. A. Leitgeb, C. K. Hitzenberger, and A. F. Fercher, "*Performance of Fourier domain vs. time domain optical coherence tomography,*" *Optics Express*, Vol. 11, pp. 889-894 (2003); M. A. Choma, M. V. Sarunic, C. Yang, and J. A. Izatt, "*Sensitivity advantage of swept source and Fourier domain optical coherence tomography,*" *Optics Express*, Vol. 11, pp. 2183-2189 (2003); R. A. Leitgeb, C. K. Hitzenberger, A. F. Fercher, and T. Bajraszewski, "*Phase-shifting algorithm to achieve high-speed long-depth-range probing by frequency domain optical coherence tomography,*" *Opt. Lett.*, Vol. 28, pp. 2201-2203 (2003); R. A. Leitgeb et al. "*Ultrahigh resolution Fourier domain optical coherence tomography,*" *Optics Express*, Vol. 12, pp. 2156-2165 (2004).

FIGS. 1A and 1B schematically illustrate two OCT configurations for use with the two major techniques of OCT, time-domain OCT and frequency-domain OCT, respectively. In both time-domain OCT and frequency-domain OCT, a broadband light source 10, such as a superluminescent diode, a mode-locked laser, or even a supercontinuum generating fiber, feeds an interferometer 20, typically a Michelson interferometer. A reference broadband mirror 30 is placed on one arm of the interferometer 20, and the tissue 40 is on the other arm of the interferometer. In the OCT configurations of FIGS. 1A and 1B, the light source is split into two fields using a beam splitter 50 or a fiber coupler (FC), and each field is directed towards one arm of the interferometer 20. The reflected light from the tissue 40 and from the reference mirror 30 are combined collinearly at the detector 60. The basic difference between time-domain OCT and frequency-domain OCT is that in time-domain OCT, the reference mirror 30 is a movable mirror, which is scanned as a function of time during the image acquisition. However, in the frequency-domain OCT, there are no moving parts, and at the detector end, the spectrum of the interference between the two reflected signals coming from each arm of the interferometer is recorded by means of an optical spectrum analyzer (OSA), e.g., a charged-coupled-device (CCD) array with the appropriate imaging optics. There are significant advantages of frequency-domain OCT over time-domain OCT, such as higher speed and higher sensitivity.

SUMMARY OF THE INVENTION

In certain embodiments, a method determines the complex scattering function of a portion of a sample under analysis. The method comprises providing a magnitude spectrum of a complex spatial Fourier transform of a complex intermediate function. The complex intermediate function is dependent on the complex scattering function of the portion of the sample under analysis. The magnitude spectrum is obtained from power spectrum data of frequency-domain optical coherence tomography of the portion of the sample under analysis. The method further comprises providing an estimated phase term of the complex spatial Fourier transform. The method further comprises multiplying the magnitude spectrum and the estimated phase term together to generate an estimated complex spatial Fourier transform. The method further comprises calculating an inverse Fourier transform of the estimated complex spatial Fourier transform. The inverse Fourier transform of the estimated complex spatial Fourier transform is a spatial function. The method further comprises calculating an estimated intermediate function by applying at least one constraint to the inverse Fourier transform of the estimated complex spatial Fourier transform.

In certain embodiments, a computer system comprises means for obtaining a magnitude spectrum of a complex spatial Fourier transform of a complex intermediate function. The complex intermediate function is dependent on the complex scattering function of a portion of a sample under analysis. The magnitude spectrum is obtained from power spectrum data of frequency-domain optical coherence tomography of the portion of the sample under analysis. The computer system further comprises means for estimating an estimated phase term of the complex spatial Fourier transform. The computer system further comprises means for multiplying the magnitude spectrum and the estimated phase term together to generate an estimated complex spatial Fourier transform. The computer system further comprises means for calculating an inverse Fourier transform of the estimated complex spatial Fourier transform. The inverse Fourier transform of the estimated complex spatial Fourier transform is a spatial function. The computer system further comprises means for calculating an estimated intermediate function by applying at least one constraint to the inverse Fourier transform of the estimated complex spatial Fourier transform.

In certain embodiments, an apparatus measures a frequency-domain optical coherence tomography power spectrum from a sample. The apparatus comprises a broadband light source. The apparatus further comprises an optical spectrum analyzer. The apparatus further comprises a partially reflective element optically coupled to the light source, to the optical spectrum analyzer, and to the sample. A first portion of light from the light source is reflected by the partially reflective element and propagates to the optical spectrum analyzer. A second portion of light from the light source propagates through the partially reflective element, impinges the sample, reflects from the sample, and propagates to the optical spectrum analyzer.

BRIEF DESCRIPTION OF THE DRAWINGS

FIGS. 1A and 1B represent prior art.

DETAILED DESCRIPTION OF THE PREFERRED EMBODIMENT

In certain embodiments described herein, the concept of minimum-phase functions is applied to improve optical coherence tomography systems. Certain embodiments described herein advantageously provide a simple processing technique for the conventional frequency-domain OCT configuration that enables a better signal-to-noise ratio, an improved measurement range, and that requires a lower-resolution optical spectrum analyzer than the currently existing processing techniques. Certain embodiments described herein rely on the property of minimum-phase functions (MPFs) to advantageously allow a function, complex or real, to be recovered from only its Fourier transform (FT) magnitude data.

Certain embodiments described herein are useful in computer-implemented analyses of the complex field scattering function of frequency-domain OCT. The general-purpose computers used for such analyses can take a wide variety of forms, including network servers, workstations, personal computers, mainframe computers and the like. The code which configures the computer to perform such analyses is typically provided to the user on a computer-readable medium, such as a CD-ROM. The code may also be downloaded by a user from a network server which is part of a local-area network (LAN) or a wide-area network (WAN), such as the Internet.

The general-purpose computer running the software will typically include one or more input devices, such as a mouse, trackball, touchpad, and/or keyboard, a display, and computer-readable memory media, such as random-access memory (RAM) integrated circuits and a hard-disk drive. It will be appreciated that one or more portions, or all of the code may be remote from the user and, for example, resident on a network resource, such as a LAN server, Internet server, network storage device, etc. In typical embodiments, the software receives as an input a variety of information concerning the material (e.g., structural information, dimensions, previously-measured magnitudes of reflection or transmission spectra).

Figure 1A:
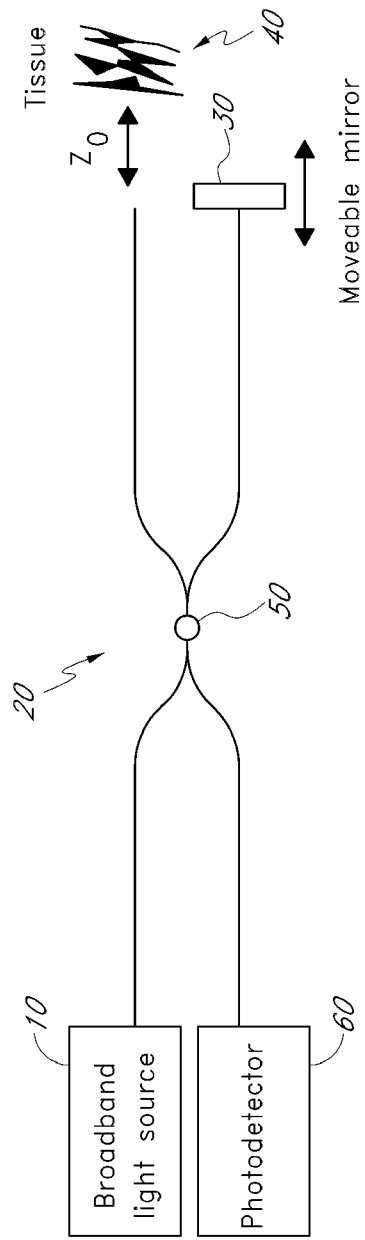
FIGS. 1A and 1B schematically illustrate two OCT configurations for use with the two major techniques of OCT, time-domain OCT and frequency-domain OCT, respectively.
Figure 1B:
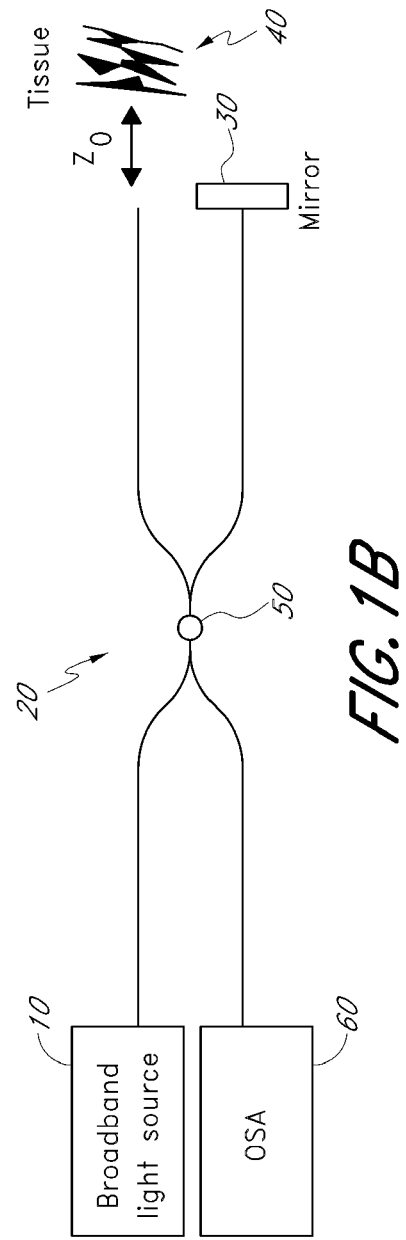

In typical OCT configurations, such as those shown in FIGS. 1A and 1B, the effective complex scattering function, which includes in its definition both the tissue 40 and the reference mirror 30, either is a minimum-phase function (MPF) or is close to being one. In certain embodiments described herein, this property allows the effective complex scattering function to be recovered by means of either the analytical Hilbert transformation or the iterative processing of the measured power spectrum data.

In the frequency-domain OCT configuration schematically illustrated by FIG. 1B, the complex field scattering function (sometimes also called the scattering potential) of the tissue of interest is $f(z)$, where z is simply the depth into the tissue, with $z \geq 0$ defining the tissue. The spectral intensity distribution of the broadband source is S(k), where $k = 2\pi/\lambda$ and $\lambda$ is the wavelength of light. In the following description, the notation is close to that given by G. Hausler and M. W. Lindler, "*Coherence radar and spectral radar—New tools for dermatological diagnosis,*" *J. Biomed. Opt.*, Vol. 3, pp. 21-31 (1998). The power spectrum detected at the optical spectrum analyzer (OSA) of FIG. 1B can be written as:

$$I(k') = S(k') \cdot \left| \int_{-\infty}^{\infty} g(z') \cdot \exp(jk' 2n_T z') \cdot dz' \right|^2 \quad (1)$$

where $g(z') = R \cdot \delta(z') + f(z' - z_0)$ and is referred to herein as the intermediate function or the effective scattering function of the system, $\delta(z')$ is the spatial Dirac-delta function, $k' = k - 2\pi/\lambda_0$, $\lambda_0$ is the center frequency of S(k), R is the field reflectivity of the reference mirror, $z_0$ is the offset distance between the reference arm and the tissue arm, as shown in FIG. 1B, and $n_T$ is the refractive index of the tissue, where the dispersion of the tissue has been assumed to be negligible and is ignored, i.e., $n_T(k) \approx n_T$. This last assumption is quite safe and has also been used in other treatments of OCT. If one defines the spatial Fourier transform (FT) frequency as $f = -k' \cdot n_T / \pi$, then the expression in Eq. (1) takes the form of a Fourier transform:

$$I(f) = S(f) \cdot |G(f)|^2 \quad (2)$$

where G(f) is the spatial FT of $g(z') = R \cdot \delta(z') + f(z' - z_0)$. If S(f) is broad and smooth enough to determine the resolution of the OCT system, then $I(f) \approx s \cdot |G(f)|^2$, where s is simply a proportionality constant.

The conventional processing techniques of frequency-domain OCT measurements are based on a processing algorithm which directly takes the inverse FT of Eq. (2). Certain embodiments described herein are compared to the conventional processing techniques by assuming that $S(f)$ is broad enough to present a simple and fair comparison by assuming that, without loss of generality, the constant s has been dropped, i.e., $I(f) \approx |G(f)|^2$. This assumption will also be made for the conventional processing techniques, so it has no effect on the discussion herein and the effect of $S(f)$ on the resolution of the OCT system is not relevant to certain embodiments described herein.

In the conventional processing techniques, taking the inverse Fourier transform (IFT) of the measured OSA spectrum $(I(f) \approx |G(f)|^2)$ directly yields:

$$IFT\{|G(f)|^2\} = |R|^2 \cdot \delta(z') + A.C.\{f(z')\} + R \cdot f^*(-z-z_0) + R^* \cdot f(z-z_0) \quad (3)$$

where A.C. denotes the complex auto-correlation function, and '*' denotes the complex conjugate operation. The important term for the recovery of the tissue scattering function is the last term of Eq. (3), i.e., $R^* \cdot f(z-z_0)$. However, the A.C.$\{f(z')\}$ term in Eq. (3) is centered around $z=0$ and usually obscures $R^* \cdot f(z-z_0)$ by spatial aliasing, thereby degrading the sensitivity and the signal-to-noise ratio of the frequency-domain OCT measurements. In the conventional processing techniques, $z_0$ is chosen to be large enough such that $R^* \cdot f(z-z_0)$ is shifted in space away from the origin, thereby reducing spatial aliasing with the A.C.$\{f(z')\}$ term. For example, for a broadband source with a coherence length of about 40 micrometers, a value of $z_0 > 200$ micrometers would be sufficient to significantly avoid the spatial overlap. By filtering the $R^* \cdot f(z-z_0)$ term around $z=z_0$, the complex scattering potential of the tissue of interest, $f(z)$, is recovered. However, choosing $z_0$ to be large enough to avoid spatial aliasing introduces other problems. For example, large values of $z_0$ cause the fringes observed in the OSA spectrum to get closer to one another, which can become a significant problem, especially for a low-resolution OSA. Furthermore, in general, a large value of $z_0$ reduces the accessible depth information in the tissue for a given OSA in the OCT configuration.

Certain embodiments described herein utilize a simple processing technique that is based on minimum-phase functions (MPFs) to improve the resolution, the signal-to-noise ratio, and the measurement range of the recovered images in frequency-domain OCT systems. The intermediate function $g(z') = R \cdot \delta(z') + f(z'-z_0)$ in an OCT system is close to an MPF, if not an exact MPF.

For the intermediate function $g(z') = R \cdot \delta(z') + f(z'-z_0)$, relevant to the power spectrum measurement of OCT, tissue typically has $n_T \approx 1.5$, so $\max\{|f(z')|\} << 1$ (where $\max\{|f(z')|\}$ is the maximum magnitude of the tissue scattering function), whereas R is approximately equal to 1. Therefore in such configurations, the intermediate function $g(z') = R \cdot \delta(z') + f(z'-z_0)$ has a dominant peak at the origin, so $g(z')$ either is close to an MPF or is an exact MPF. In certain embodiments, this property of the intermediate function $g(z')$ is used to uniquely recover the tissue scattering function $f(z)$ from only the knowledge of $|G(f)|$, regardless of the value of $z_0$. In certain embodiments in which the condition of $\max\{|f(z')|\} << 1$ is not satisfied, more power can be directed to the reference arm to make R larger, and hence to have a dominant peak at the origin for $g(z') = R \cdot \delta(z') + f(z'-z_0)$.

It is generally not possible to fully recover a one-dimensional function from the knowledge of its FT magnitude alone. However, there are families of functions which are exceptions to this rule for which the FT phase can be recovered from the FT magnitude alone, and visa versa. One exemplary such family is the family of minimum-phase functions (MPFs). An MPF is characterized by having a z-transform with all its poles and zeros either on or inside the unit circle. As a result of this property, the FT phase and the logarithm of the FT magnitude of an MPF are Hilbert transforms of one another. See, e.g., V. Oppenheim and R. W. Schafer, "*Digital Signal Processing*," (Prentice Hall, 2002), Chap. 7; T. F. Quatieri, Jr., and A. V. Oppenheim, "*Iterative techniques for minimum phase signal reconstruction from phase or magnitude*," IEEE Trans. Acoust., Speech, Signal Processing, Vol. 29, pp. 1187-1193 (1981); M. Hayes, J. S. Lim, and A. V. Oppenheim, "*Signal reconstruction from phase or magnitude*," IEEE Trans. Acoust., Speech, Signal Processing, Vol. 28, pp. 672-680 (1980). Consequently, an MPF can be calculated from only its FT amplitude.

In certain embodiments, this recovery of the function of interest (e.g., the intermediate function $g(z') = R \cdot \delta(z') + f(z'-z_0)$) can be obtained from only its FT amplitude (e.g., $|G(f)|$) by first taking the Hilbert transform of the logarithm of the function's FT magnitude (e.g., the logarithmic Hilbert transform of the function's FT magnitude) to obtain the FT phase, and then inverting the full complex FT. However, this direct approach is not the preferred solution because of difficulties in its numerical implementation, in particular phase unwrapping. In certain embodiments, an iterative error-reduction technique is used, as described more fully below.

A second approach for the recovery of the function of interest (e.g., the intermediate function $g(z') = R \cdot \delta(z') + f(z'-z_0)$) is to use an iterative error-reduction method. Examples of iterative error-reduction methods include, but are not limited to, those described by J. R. Fienup, "*Reconstruction of an object from the modulus of its Fourier transform*," Opt. Lett., Vol. 3, pp. 27-29 (1978) or R. W. Gerchberg and W. O. Saxton, "*Practical algorithm for the determination of phase from image and diffraction plane pictures*," Optik, Vol. 35, pp. 237-246 (1972).

Figure 2:
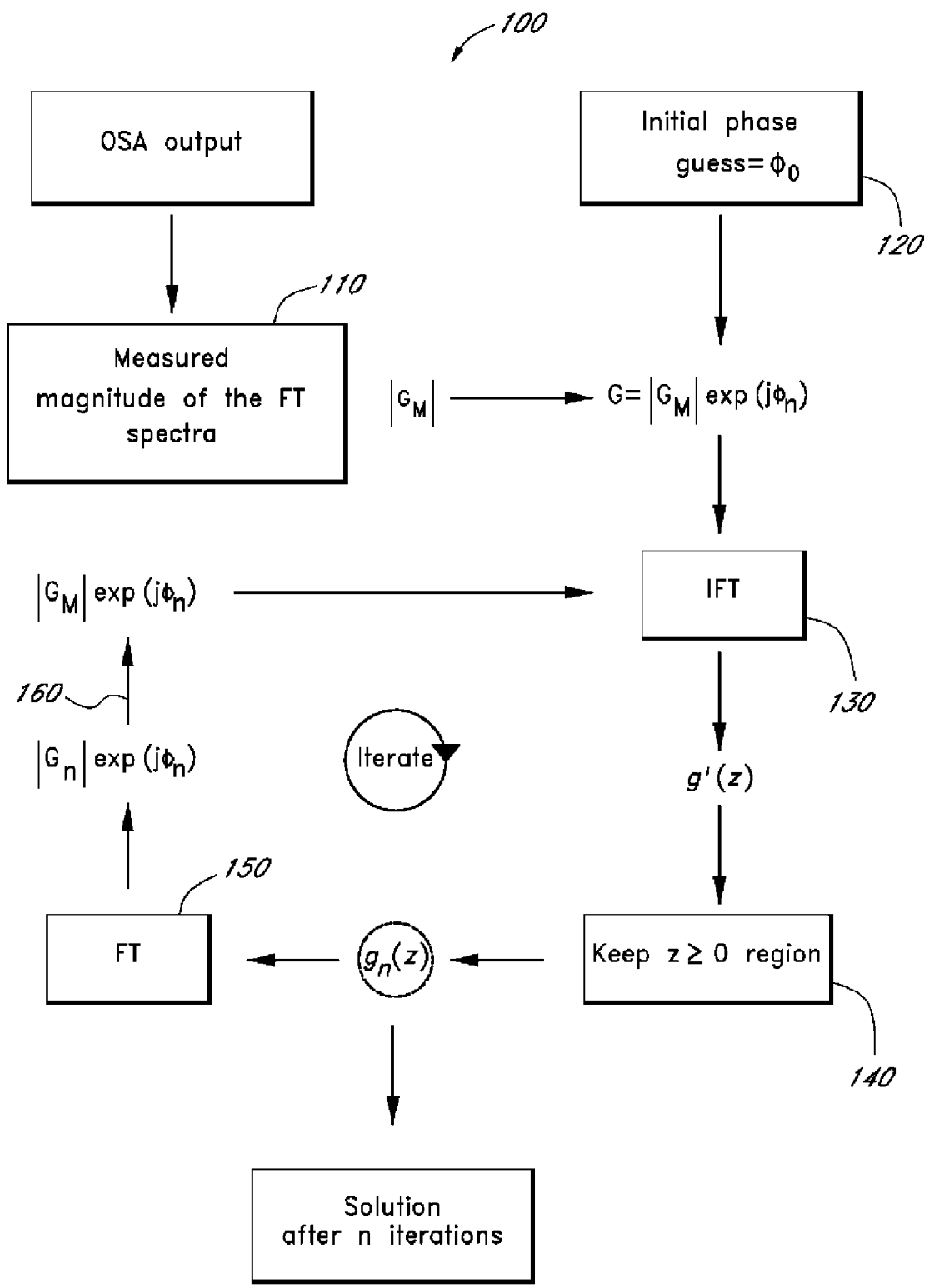
FIG. 2 is a flow diagram of an example iterative error-reduction method for determining the complex scattering function $f(z)$ of a sample in accordance with certain embodiments described herein.

FIG. 2 is a flow diagram of an exemplary iterative error-reduction method 100 for determining the complex tissue scattering function $f(z)$ of a portion of a sample under analysis in accordance with certain embodiments described herein. This iterative error-reduction method 100 involves using a known (e.g., measured) magnitude spectrum $|G(f)|$ of a complex spatial Fourier transform of a complex intermediate function $g(z')$, together with known properties of this function (e.g., that it is a real function or a causal function), to correct an initial guess of the intermediate function $g(z')$. In certain embodiments, this correction is done iteratively. In certain embodiments, the intermediate function $g(z')$ is dependent on the complex tissue scattering function $f(z)$ of the sample, as described more fully below.

In certain embodiments, the only quantity that is fed into the method 100 is the magnitude spectrum $|G_M(f)|$ of the complex spatial FT of the complex intermediate function $g(z')$, where the subscript M denotes that this magnitude spectrum is a measured quantity, as shown by the operational block 110. In certain embodiments, providing the magnitude spectrum $|G_M(f)|$ corresponding to the intermediate function $g(z')$ comprises measuring a frequency-domain OCT power spectrum from the portion of the sample under analysis and calculating the square-root of the measured frequency-domain OCT power spectrum to yield the measured FT magnitude spectrum $|G_M(f)|$. In certain other embodiments, providing the magnitude spectrum $|G_M(f)|$ comprises providing a previously-measured frequency-domain OCT power spectrum and calculating the square-root of the previously-measured frequency-domain OCT power spectrum or providing the square-root of a previously-measured frequency-domain OCT power spectrum.

Since the FT phase term is missing from the measurement, an initial guess for the phase, $\phi_0(f)$, is used to provide an estimated phase term $\exp(j\phi_0)$ in the operational block 120. In certain embodiments, this initial guess does not significantly affect the accuracy of the result of the convergence of the method 100. For this reason, the initial guess for the phase $\phi_0(f)$ can be conveniently chosen to equal zero (e.g., $\phi_0(f)=0$) or some other real or complex constant (e.g., $\pi$, $\pi/2$). In certain embodiments, the initial guess for the phase can be a previously-stored function $\phi_0(f)$ retrieved from the computer system. In certain embodiments, the initial guess for the phase can be a phase obtained from a different portion of the sample. For example, in tissue imaging, the initial guess for the phase $\phi_0(f)$ can be a phase resulting from a portion of the tissue adjacent to the portion of the surface under analysis. Thus, in a real imaging situation, the initial guess for the phase $\phi_0(f)$ can be dynamically assigned to be the new phase resulting from a previous measurement. In certain embodiments, the initial guess for the phase can be calculated from the measured magnitude spectrum $|G_M(f)|$ using a logarithmic Hilbert transform.

In certain embodiments, the magnitude spectrum and the estimated phase term are multiplied together to generate an estimated complex spatial Fourier transform $|G_M|\cdot\exp(j\phi_0)$. The inverse Fourier transform (IFT) of $|G_M|\cdot\exp(j\phi_0)$ is then computed numerically, as shown by the operational block 130, to calculate an inverse Fourier transform $g'(z)$ of the estimated complex spatial Fourier transform, wherein the inverse Fourier transform $g'(z)$ is a spatial function. In certain embodiments, the operational block 140 comprises applying at least one constraint to the inverse Fourier transform $g'(z)$ to calculate an estimated intermediate function $g_1(z)$. In certain embodiments in which the sample has a known spatial extent, applying the at least one constraint comprises setting the IFT to zero for regions outside the known spatial extent of the sample. For example, since $g'(z)$ approximates a minimum-phase function (MPF) and since MPFs are causal, only the $z \geq 0$ portion of $g'(z)$ is retained (e.g., the causality condition), and all values of $g'(z)$ for $z<0$ are set to zero, thereby producing a new function $g_1(z)$.

In certain embodiments in which the intermediate function $g(z)$ has a known spatial extent (e.g., to be less than 1 millimeter deep), the operational block 140 can also include setting the inverse Fourier transform $g'(z)$ to zero for regions outside the known spatial extent of the intermediate function $g(z)$ by inserting zeros for z greater than this limit (e.g., $z>1$ millimeter) to produce the function $g_1(z)$, thereby advantageously speeding up convergence of the error-reduction method. In certain embodiments, the new function $g_1(z)$ provided by the operational block 140 serves as a first estimate of the complex MPF (i.e., the estimated intermediate function $g(z)$).

In certain embodiments, the FT of the estimated intermediate function $g_1(z)$ is calculated in the operational block 150, thereby providing a new calculated phase $\phi_1(f)$ (hence a new calculated phase term $\exp(j\phi_n)$) and a new magnitude spectrum $|G_1(f)|$ for the FT of the estimated intermediate function $g_1(z)$. In certain embodiments, the calculated FT magnitude spectrum $|G_1(f)|$ is replaced by the measured magnitude spectrum $|G_M(f)|$, as shown by the arrow 160. In certain embodiments, the loop is then repeated using the measured magnitude spectrum $|G_M(f)|$ and the calculated phase term $\exp(j\phi_1)$ as the new input function in the operational block 130, which provides a second function $g_2(z)$. In certain embodiments, only a single iteration is used, while in other embodiments, this loop is repeated until convergence is achieved. In certain embodiments, convergence is defined to be achieved when the difference between consecutive estimates of the function $\int |g_n(z)-g_{n-1}(z)|^2 \, dz / \int |g_n(z)|^2 \, dz$ is less than a predetermined value, for example 0.1%. In certain embodiments, less than 100 iterations are adequate for achieving convergence, taking less than a second to compute using a rather slow programming environment such as MATLAB 5 on a 500 MHz computer with $2^9$ data points. In certain embodiments, applying the constraint in the operational block 140 advantageously reduces the number of iterations which achieve convergence.

In certain other embodiments, the loop is repeated a predetermined number of times (e.g., 100). In certain embodiments, the predetermined number of times is selected to be sufficiently large so that the method achieves, or is close to achieving, convergence. In certain embodiments, at the end of the n-th iteration, $g_n(z)$ is the recovered complex MPF. In certain other embodiments, the iterations of the loop are stopped when the user (e.g., the doctor reviewing the OCT images) determines that the image quality is sufficient.

Empirical results indicate that such iterative error-reduction methods converge to the minimum-phase function corresponding to a given FT magnitude. (See, e.g., T. F. Quatieri, Jr., and A. V. Oppenheim, "*Iterative techniques for minimum phase signal reconstruction from phase or magnitude*," IEEE Trans. Acoust., Speech, Signal Processing, Vol. 29, pp. 1187-1193 (1981); A. Ozcan et al., "*Iterative processing of second-order optical nonlinearity depth profiles*," Opt. Express, Vol. 12, pp. 3367-3376 (2004); A. Ozcan et al., "*Group delay recovery using iterative processing of amplitude of transmission spectra of fibre Bragg gratings*," Electron. Lett., Vol. 40, pp. 1104-1106 (2004).) In other words, for the infinite family of FT phase functions that can be associated with a known (e.g., measured) FT magnitude, certain embodiments described herein converge to the one and only one FT phase function that has the minimum phase. Since this solution is unique, if it is known a priori that the function to be reconstructed is an MPF (or that the function approximates an MPF), then the solution provided by the error-reduction method is the correct function.

To understand intuitively which physical functions such as $g(z')$ are likely to be minimum-phase functions, $g_{min}(n)$ is used to denote an MPF, where n is an integer that numbers sampled values of the function variable (e.g., space z' for the tissue scattering potential $g(z')$). Because all physical MPFs are causal, $g_{min}(n)$ must be equal to zero for $n<0$. As discussed by V. Oppenheim and R. W. Schafer in "*Digital Signal Processing*," (Prentice Hall, 2002), Chap. 7, the energy of a minimum-phase function, which is defined as $$\sum_{n=0}^{m-1} |g_{min}(n)|^2$$

for m samples of the function, satisfies the following inequality:

$$\sum_{n=0}^{m-1} |g_{min}(n)|^2 \geq \sum_{n=0}^{m-1} |g(n)|^2 \qquad (4)$$

for all possible values of m>0. In Eq. (4), g(n) represents any of the functions that have the same FT magnitude as $g_{min}(n)$. This property suggests that most of the energy of $g_{min}(n)$ is concentrated around n=0. Stated differently, any function, complex or real, with a dominant peak around n=0 (i.e., close to the origin) will be either a minimum-phase function or close to one, and thus the function will work extremely well with iterative error-reduction methods in accordance with certain embodiments described herein. Although there may be other types of MPFs besides functions with a dominant peak, this class of MPFs can be used as described herein because they are straightforward to construct with OCT data and because they yield exceedingly good results. See, also, A. Ozcan, M. J. F. Digonnet, and G. S. Kino, "*Iterative processing of second-order optical nonlinearity depth profiles,*" Opt. Express, Vol. 12, pp. 3367-3376 (2004).

Recovering $f(z)$ from only the knowledge of $|G(f)|$ using error-reduction methods compatible with certain embodiments described herein advantageously provides significant advantages in frequency-domain OCT over the conventional processing approaches. In certain embodiments, the error-reduction method does not utilize a minimum constraint for $z_0$, so $z_0$ can conveniently be chosen close to zero. Such embodiments provide a significant improvement on the resolution requirement of the OSA of the OCT system. Furthermore, since the depth measurement range into the tissue is inversely proportional to the maximum spatial frequency measured in the OSA spectrum, in principle, a value of $z_0$ close to zero allows a larger measurement range for the OCT configuration. In certain embodiments, the error-reduction method deals with the square-root of the measured power spectrum $\sqrt{I(k')}$, whereas the conventional approaches take a direct IFT of I(k'). In terms of noise sensitivity, in certain such embodiments, the error-reduction method performs much better than the conventional approach, since the noise term in I(k') is much stronger than in $\sqrt{I(k')}$. For example, by adding some random noise to $\sqrt{I(k')}$, i.e., $\sqrt{I(k')}$+noise, the added noise term becomes stronger, i.e., $\sim 2 \cdot \sqrt{I(k')} \cdot$noise. In certain embodiments, the error-reduction method advantageously avoids the degradation in the signal-to-noise ratio in the classical processing techniques associated with the spatial aliasing due to the A.C.{$f(z')$} term in Eq (3), thereby yielding a better performance.

Figure 3A:
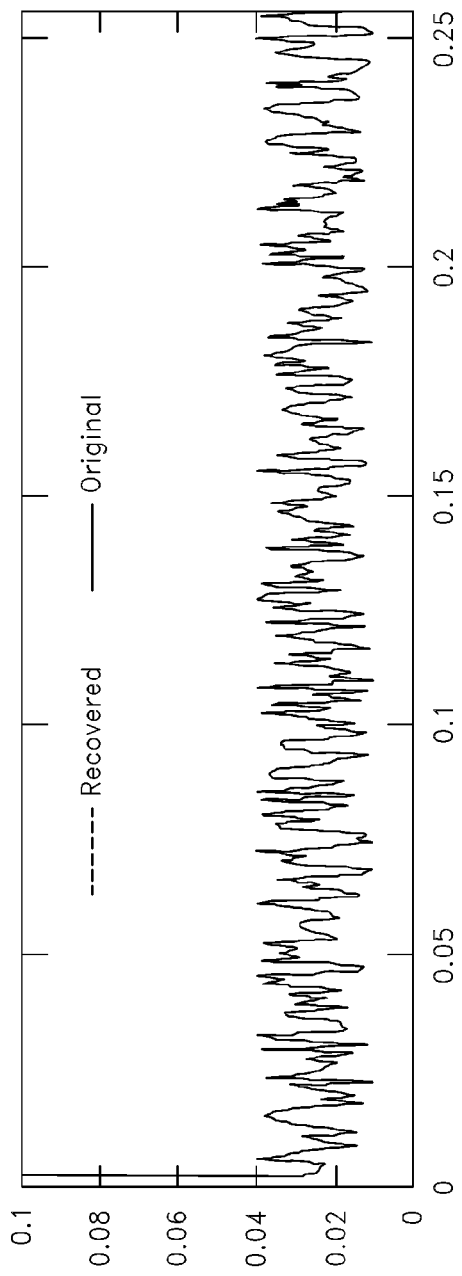
FIGS. 3A and 3B are graphs of the magnitude and phase, respectively, of an example simulated complex tissue scattering function (solid lines) and a recovered complex tissue scattering function (dashed lines).
Figure 3B:
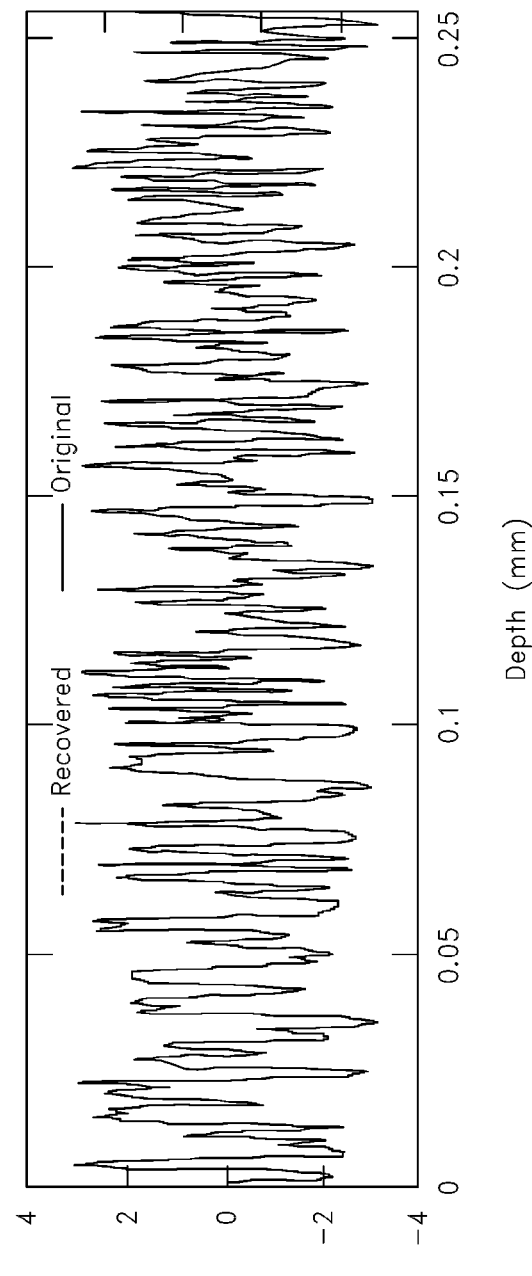

In an example numerical simulation, to simulate a rather challenging problem, the complex tissue scattering function is simulated to be a uniform random variable, both in magnitude and phase, as shown by solid lines in FIGS. 3A and 3B, respectively. In this example numerical simulation, it is assumed that $z_0$=0, which means that the length of the upper arm is roughly matched to the length of the lower arm of the Michelson interferometer in the OCT configuration schematically illustrated by FIG. 1B. The field reflectivity of the tissue is allowed to vary in magnitude between 0.01 and 0.04. These numbers are not critical, and could as well be chosen to be rather different. For the same example simulation, the mirror reflectivity R used in the OCT configuration was chosen to be equal to 1, which is the source of the sharp peak observed in the scattering function shown in FIG. 3A. The whole cross-section of the tissue is assumed to be about 0.25 millimeter, and this value could as well be chosen larger or smaller without any change in the results.

Figure 4:
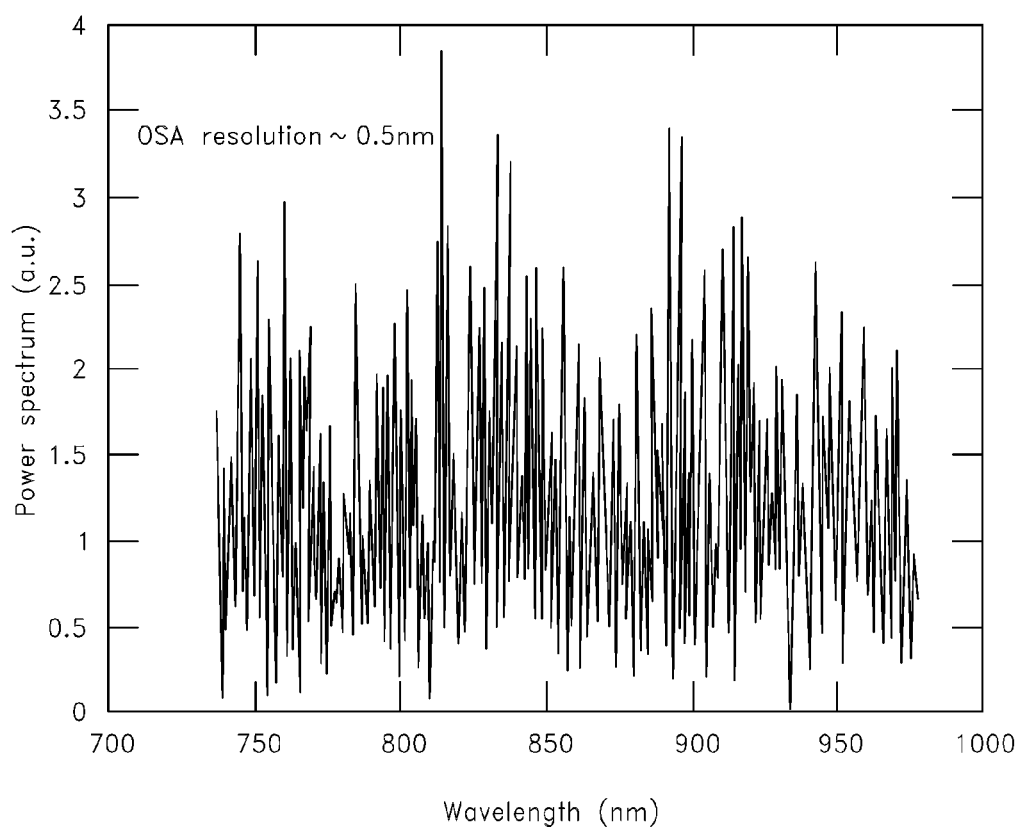
FIG. 4 is a graph of the computed power spectrum, i.e., the square of the Fourier transform magnitude of the simulated tissue scattering function of FIGS. 3A and 3B.

FIG. 4 is a graph of the computed power spectrum, i.e., the square of the FT magnitude of the simulated scattering function shown in FIGS. 3A and 3B. For this computation, a resolution of about 0.5 nanometer was assumed for the OSA, and a center wavelength of 840 nanometers was assumed for the broadband source. The whole trace shown in FIG. 4 has only 512 data points. Feeding the square-root of the power spectrum shown in FIG. 4 to the iterative error-reduction method 100 shown by FIG. 2 yields a recovered complex tissue scattering function as shown by the dashed lines in FIGS. 3A and 3B. The recovery for both the magnitude and the phase of the tissue scattering function is so good that the recovered curves cannot be distinguished from the originally simulated curves, as shown in FIGS. 3A and 3B. The calculation of the recovered curves took less than a second using MATLAB 5 on a 500-MHz computer, which suggests that by using a faster programming environment such as C++, together with a faster processor, sub-millisecond computation times can be achieved.

Figure 5A:
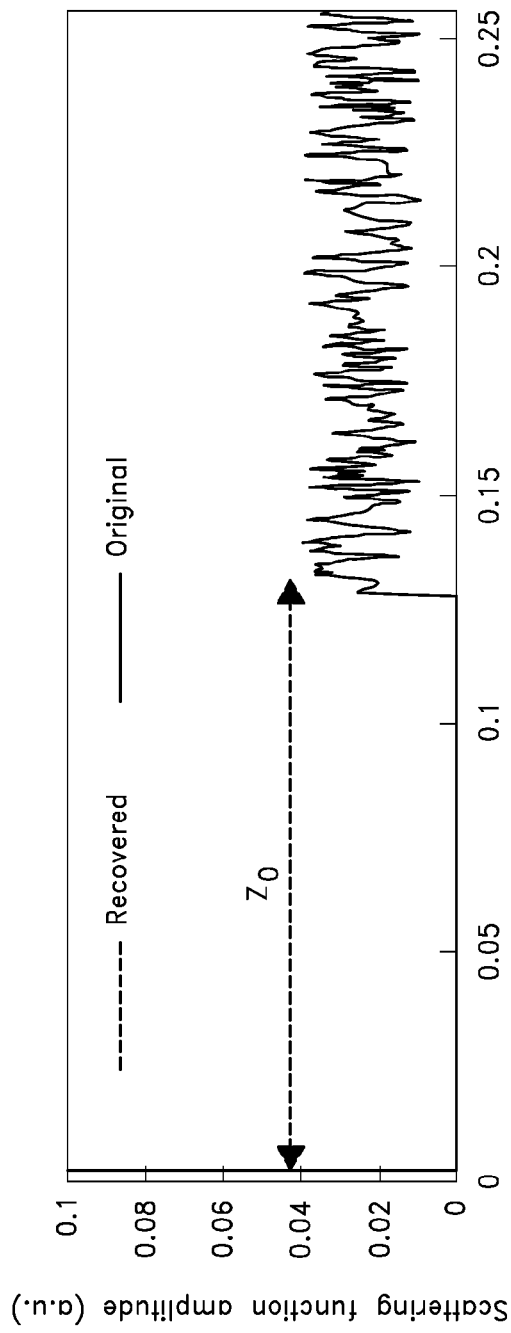
FIGS. 5A and 5B show the magnitude and phase, respectively, of the simulated tissue scattering function (solid lines) and the recovered tissue scattering function (dashed lines) for another example simulation in which $z_0$ equals about 1.2 millimeters.
Figure 5B:
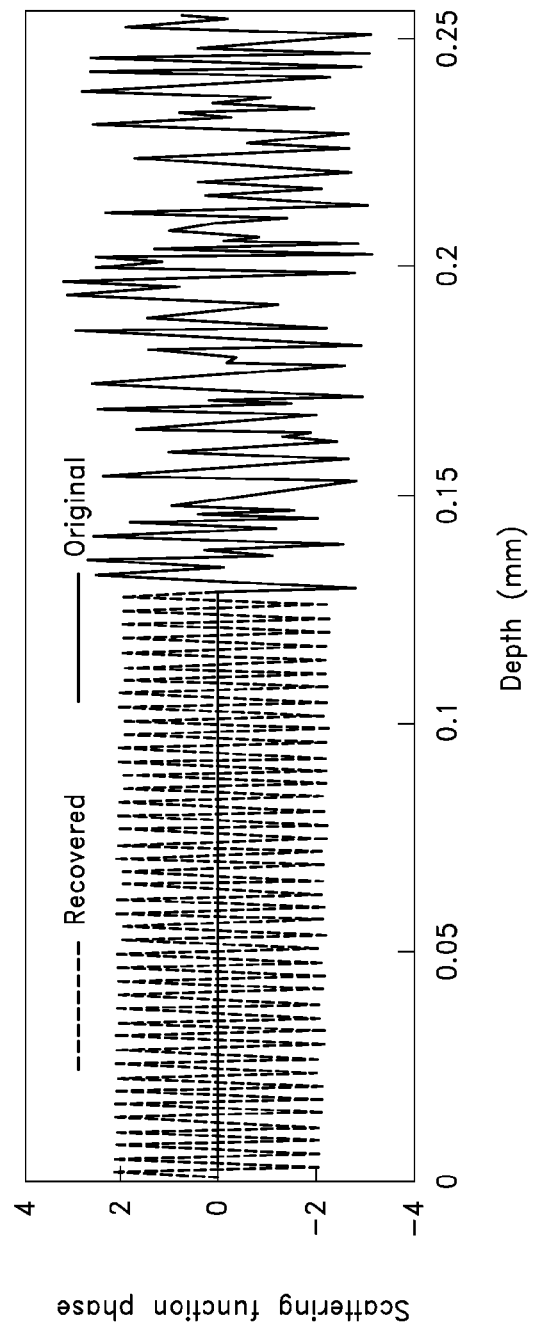
Figure 6:
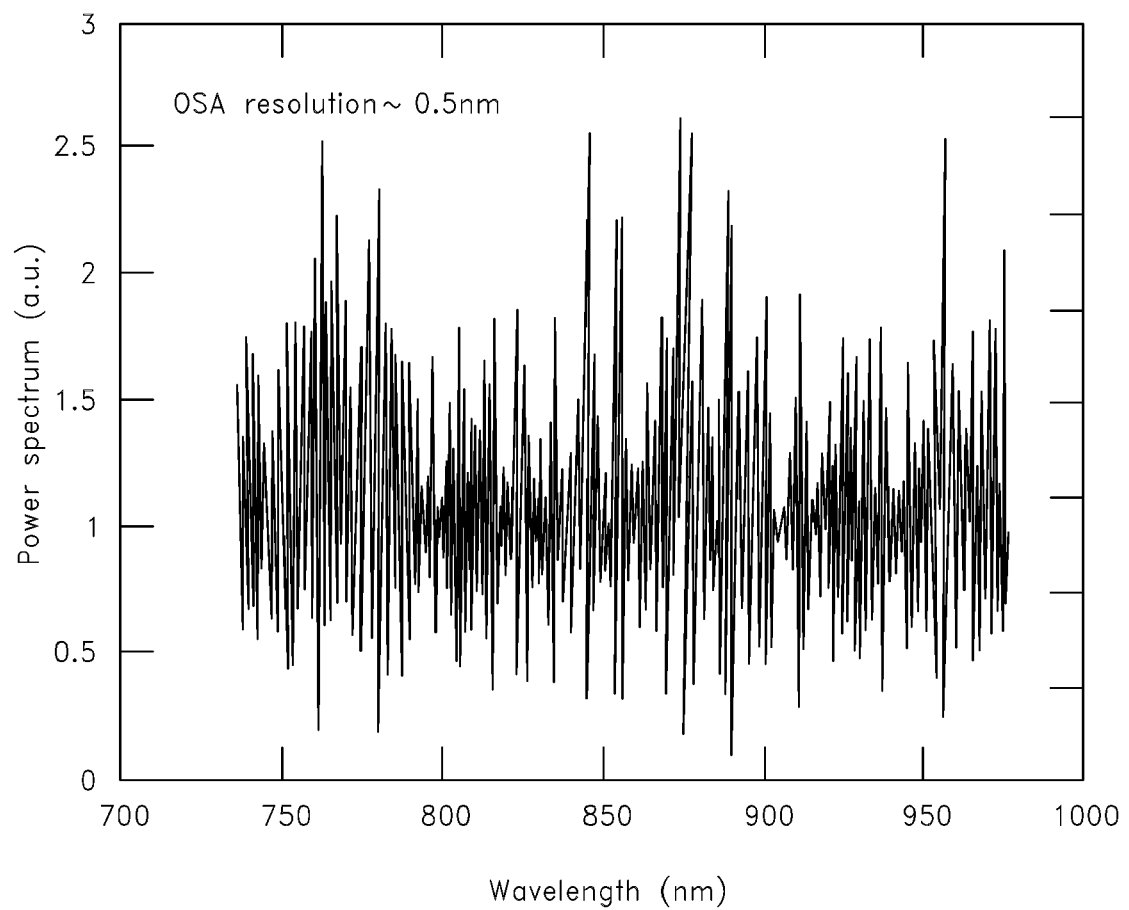
FIG. 6 is a graph of the computed power spectrum of the simulated complex tissue scattering function of FIGS. 5A and 5B.

The solid lines of FIGS. 5A and 5B show the magnitude and phase, respectively, of the tissue scattering function for another example numerical simulation in which $z_0$ equals about 0.12 millimeter. The other parameters of this simulation were assumed to be the same as in the example of FIGS. 3A, 3B, and 4. FIG. 6 is a graph of the computed power spectrum of the simulated complex tissue scattering function of FIGS. 5A and 5B. Due to $z_0$=~0.12 millimeter, the frequency of fringes in the power spectrum gets more rapid, as shown by a comparison of FIGS. 4 and 6. Feeding the square-root of the power spectrum of FIG. 6 to the iterative error-reduction method 100 of FIG. 2 yields a recovered complex tissue scattering function as shown by the dashed lines of FIGS. 5A and 5B. The recovery is again excellent, with the recovered complex tissue scattering function between about 0.12 millimeter and about 0.25 millimeter nearly indistinguishable from the simulated complex tissue scattering function. In the gap region, e.g., between 0 and 0.12 millimeter, the recovered phase of the tissue scattering function can simply be ignored since the magnitude of the function in that interval is zero, making the definition of a definite phase meaningless in the gap region.

Figures 7A, 7B:
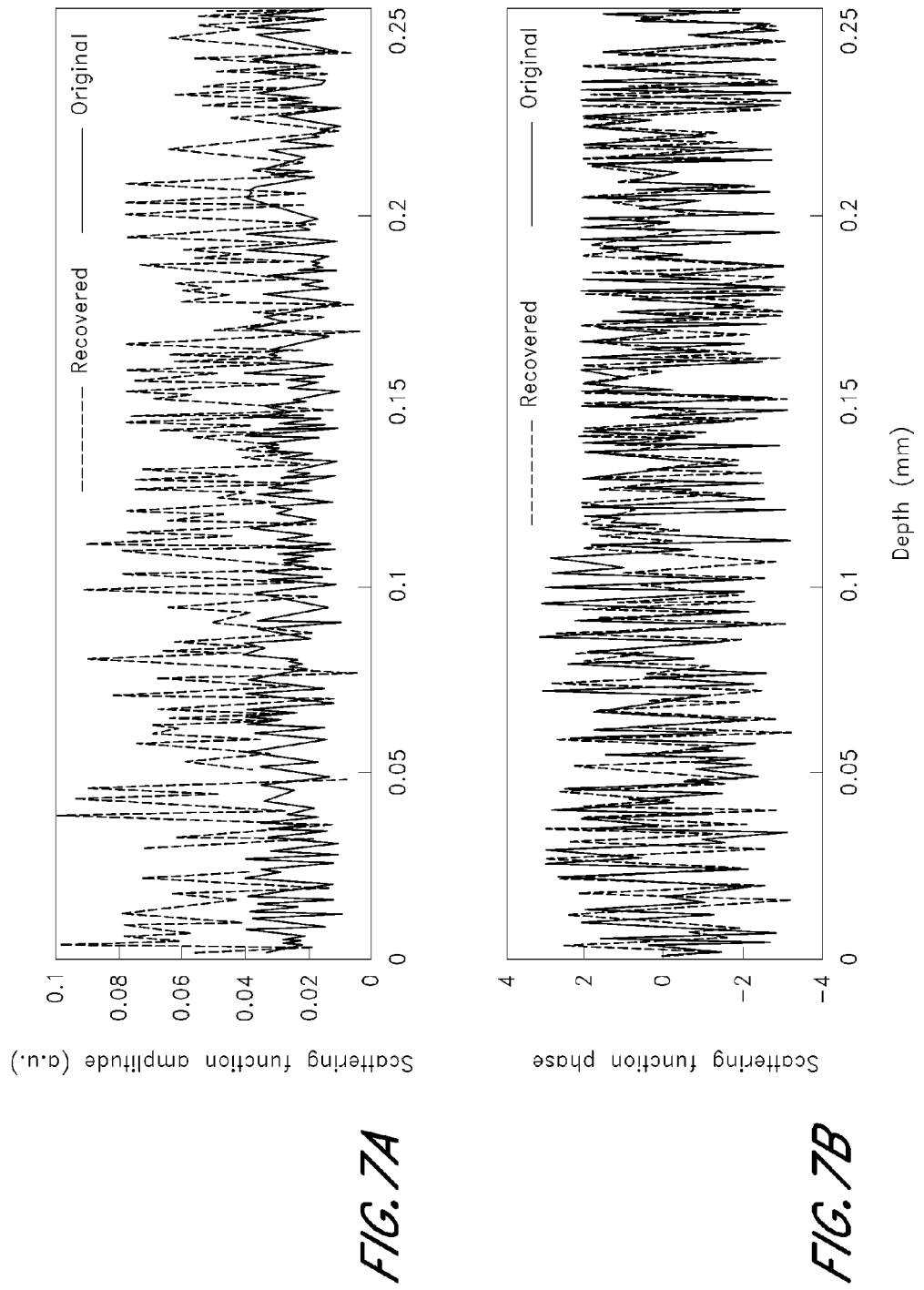
FIGS. 7A and 7B show the magnitude and phase, respectively, of an example simulated tissue scattering function (solid line) and a recovered tissue scattering function (dashed line) for a ratio of $R/\max\{|f(z')|\}$ approximately equal to 5.

The parameter of the ratio of R to max{$|f(z')|$} indicates how close the effective complex scattering function $g(z')=R \cdot \delta(z')+f(z'-z_0)$, is to a true MPF. In the example numerical simulations discussed above, this ratio was chosen to be 1/0.04=25. For typical imaged tissue samples, the scattering function is quite weak, so a ratio of 25 is a reasonable assumption. However, for certain embodiments in which max{$|f(z')|$}<<1 is not satisfied, an uneven beam splitter can be used in the OCT configuration to increase this ratio. Other numerical simulations have shown that the iterative error-reduction method 100 of FIG. 2 converges for ratios of R to max{$|f(z')|$} greater than about 10. FIGS. 7A and 7B show the magnitude and phase, respectively, of a simulated tissue scattering function (solid line) and a recovered tissue scattering function (dashed line) using the iterative error-reduction method 100 of FIG. 2 for which $z_0$=0 and R is reduced to 0.2 while still keeping max{$|f(z')|$}=0.04, i.e., a ratio of 5. As shown in FIGS. 7A and 7B, the recovered tissue scattering function in this case deviates from the simulated tissue scattering function, which is due to the lower value of the R/max{$|f(z')|$} ratio.

In certain embodiments, the reference mirror used in the lower arm of the Michelson interferometer shown in FIG. 1B is a broadband mirror with a spatial scattering function which is a Dirac-delta function $\delta(z')$. In certain other embodiments, the spatial scattering function of the reference mirror is not a true delta function. In certain such embodiments, the reference mirror has a broader spatial scattering function and comprises a stacked dielectric mirror or a fiber Bragg grating. In certain embodiments in which the scattering function of the reference mirror is much narrower than the width of $f(z)$ (e.g., by a factor of 10), the iterative error-reduction method 100 illustrated by FIG. 2 still converges to the unique solution. For example, for certain embodiments in which the tissue thickness that is imaged is 1 millimeter, a reference mirror that has a spatial scattering function width of about 50 micrometers or less can be successfully used. For typical metal-coated reference mirrors, the spatial scattering function width is essentially less than a micron, so the spatial scattering function of such reference mirrors can be approximated by a true Dirac-delta function $\delta(z')$.

Figure 8:
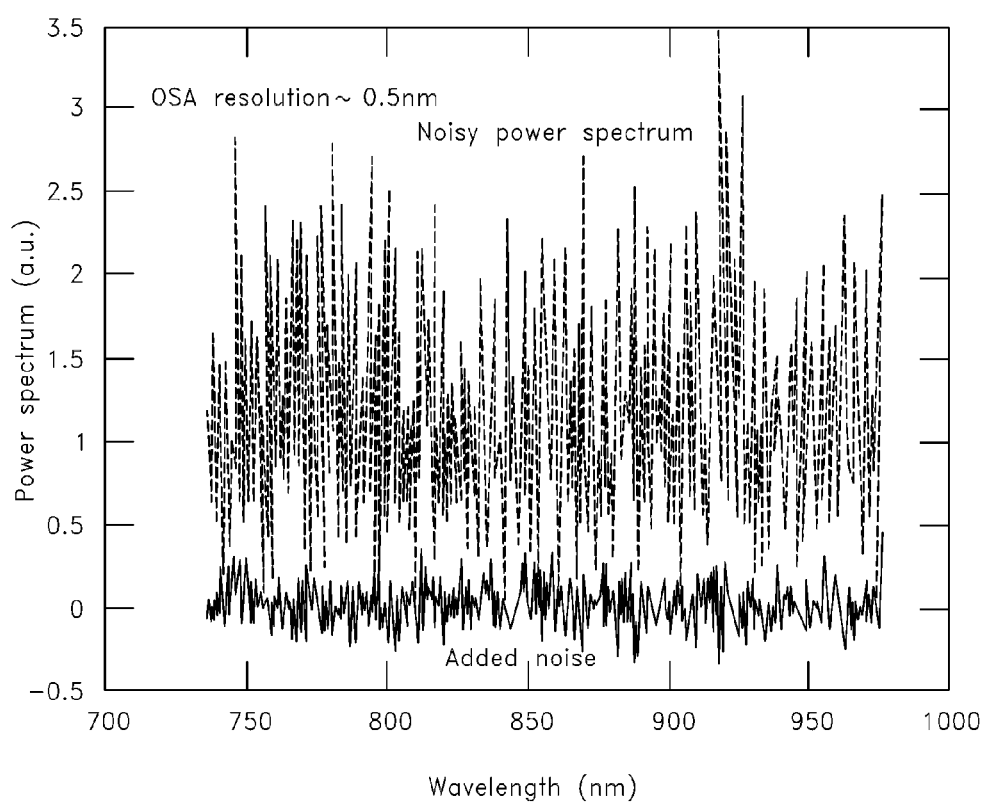
FIG. 8 is a graph of an example simulated power spectrum with an added 30% peak-to-peak amplitude uniform random noise.
Figure 9A:
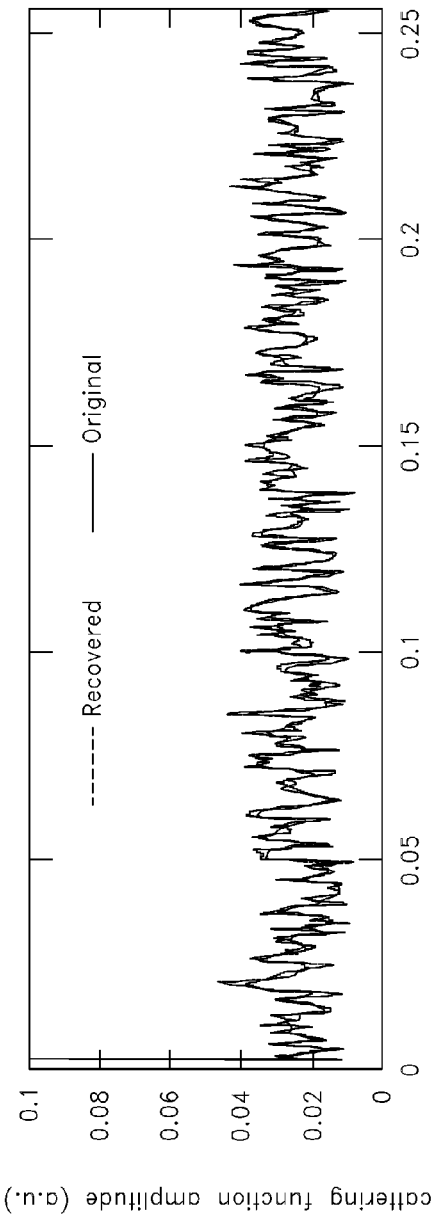
FIGS. 9A and 9B are graphs of the magnitude and phase, respectively, of the simulated tissue scattering function (solid lines) corresponding to the simulated power spectrum of FIG. 8 and the recovered tissue scattering function (dashed lines).
Figure 9B:
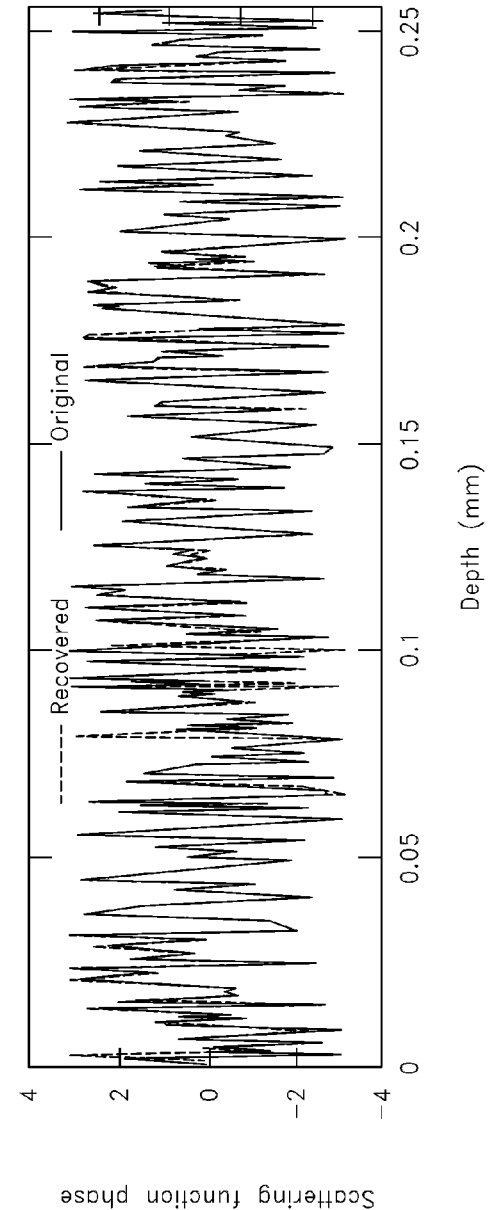

FIG. 8 is a graph of a simulated power spectrum (dashed line) with an added 30% peak-to-peak amplitude uniform random noise (solid line) to illustrate the strength in terms of noise sensitivity of certain embodiments described herein by showing how measurement errors and noise in the power spectrum affect the accuracy of the recovered tissue scattering function. The resolution of the OSA in the simulation of FIG. 8 was again limited to about 0.5 nanometer and all the other parameters of the simulation of FIG. 8 were chosen to be the same as in the simulation of FIG. 3. FIGS. 9A and 9B are graphs of the magnitude and phase, respectively, of the simulated tissue scattering function (solid lines) corresponding to the simulated power spectrum of FIG. 8 and the recovered tissue scattering function (dashed lines) using the iterative error-reduction method 100 shown by FIG. 2. As shown in FIGS. 9A and 9B, the agreement of both the magnitude and the phase between the simulated and recovered tissue scattering functions, under even 30% uniform random noise, is quite impressive. Almost all the details of the tissue scattering function have been recovered, demonstrating that in certain embodiments, the iterative error-reduction method 100 shown in FIG. 2 could confidently be used even in a fairly noisy OCT configuration.

Figure 10:
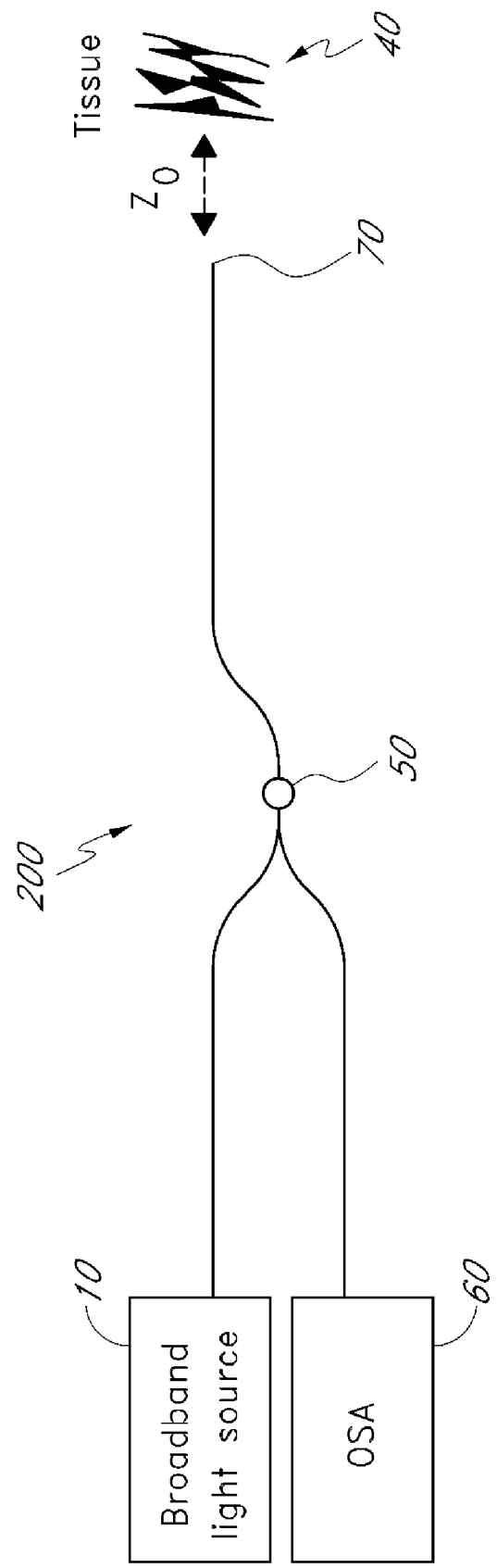
FIG. 10 schematically illustrates an example frequency-domain OCT configuration compatible with certain embodiments described herein.

FIG. 10 schematically illustrates an example frequency-domain OCT configuration 200 compatible with certain embodiments described herein which can provide a large and easily realizable $R/\max\{|\eta(z')|\}$ ratio (e.g., greater than 10) to be utilized for $g(z')=R\cdot\delta(z')+f(z'-z_0)$. The frequency-domain OCT configuration 200 schematically illustrated by FIG. 10 is simpler than the classical frequency-domain OCT configuration schematically illustrated by FIG. 1B in that the configuration 200 has a single arm extending from the fiber coupler 50 towards the sample 40. Instead of the reference mirror 30 in the lower arm of the Michelson interferometer 20 shown in FIG. 1B, the frequency-domain OCT configuration 200 uses the back reflection from a partially reflective element (e.g., the fiber end 70) as the reference signal. The partially reflective element is optically coupled to the light source 10, to the OSA 60, and to the sample 40. A first portion of light from the light source 10 is reflected by the partially reflective element and propagates to the OSA 60. A second portion of light from the light source 10 propagates through the partially reflective element, impinges the sample 40, reflects from the sample 40, and propagates to the OSA 60. In this configuration 200, the effective complex scattering function will still be of the form: $g(z')=R(z')+f(z'-z_0)$. However, for certain embodiments utilizing a bare fiber end 70 in air as the partially reflective element, R will be limited to about 0.2. In certain such embodiments, the tissue sample 40 will generate a maximum magnitude of the tissue scattering function of less than about 0.02, i.e., $\max\{|(z^1)|\} \gtrsim \sim 0.02$. In certain such embodiments, the function $g(z')=R\cdot\delta(z')+f(z'-z_0)$ will be close enough to a true MPF such that the error-reduction methods described herein can successfully be applied to uniquely image the complex tissue scattering function. In certain embodiments, the partially reflective element comprises a tilted broadband attenuator positioned between the fiber coupler 50 and the tissue sample 40 to reduce the maximum value of the measured magnitude of the tissue scattering function. In certain other embodiments, a fiber end 70 coated with a partially reflective material is used to increase the value of R. Other configurations are also compatible with embodiments described herein by providing sufficiently large ratios of $R/\max\{|f(z')|\}$ to utilize the error-reduction method described herein.

For certain embodiments in which an angled fiber end 70 is used in the configuration schematically illustrated by FIG. 10, the value of R approximates zero, such that there is no interference at the OSA. In certain such embodiments, the measured quantity will be simply the power spectrum $|F(f)|^2$ of the tissue's complex scattering function, $f(z)$. In certain embodiments, $f(z)$ will have a sharp peak close to the origin, due to the high reflection from the air-tissue interface, such that $f(z)$ approximates an MPF. Thus, in certain such embodiments, the whole complex $f(z)$ can be fully recovered from only the measurement of $|F(f)|^2$ using the analytical Hilbert transformation or the iterative error-reduction method discussed herein. In certain embodiments, this relatively simple, non-interferometric method based on MPFs advantageously provides fast imaging of most tissues. In certain embodiments, e.g., for measurements made from tissue which is a strong scattering source in deeper parts of the body, $f(z)$ would not approximate an MPF. Therefore, in such embodiments, the complex $f(z)$ would not be fully recovered from only the measurement of $|F(f)|^2$. However, an interferometric configuration in which R does not approximate zero can be used for such strongly scattering tissue, as described herein.

Various embodiments of the present invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. An apparatus for measuring a frequency-domain optical coherence tomography power spectrum from a sample, the apparatus configured to be optically coupled to a light source, the apparatus comprising:
   a partially reflective element configured to be optically coupled to the sample,
   wherein a first portion of light from the light source is configured to be reflected by the partially reflective element,
   wherein a second portion of light from the light source is configured to propagate through the partially reflective element, to impinge the sample, to reflect from the sample; and
   an analyzer configured to receive the first and second portions of light and to measure the frequency-domain optical coherence tomography power spectrum in response to the first portion of light and the second portion of light.

2. The apparatus of claim 1, further comprising an optical fiber optically coupled to the light source and the sample, the partially reflective element comprising an end of the optical fiber.

3. The apparatus of claim 2, wherein the end of the optical fiber is bare.

4. The apparatus of claim 2, wherein the end of the optical fiber is coated with a partially reflective material.

5. The apparatus of claim 2, wherein the end of the optical fiber is angled.

6. The apparatus of claim 1, wherein the partially reflective element comprises a tilted broadband attenuator.

7. The apparatus of claim 6, wherein the apparatus comprises a fiber coupler and the tilted broadband attenuator is positioned between the fiber coupler and the sample.

8. The apparatus of claim 1, wherein the apparatus further comprises a fiber coupler and a single optical fiber extending from the fiber coupler towards the sample.

9. The apparatus of claim 8, wherein the first portion of light and the second portion of light propagate along the single optical fiber extending from the fiber coupler towards the sample.

10. The apparatus of claim 9, wherein the apparatus uses the reflected first portion of light as a reference signal.

11. The apparatus of claim 1, wherein the partially reflective element has a reflectivity less than 0.2.

12. The apparatus of claim 1, wherein the partially reflective element has a reflectivity of about zero.

13. The apparatus of claim 1, further comprising a computer system, the computer system comprising:
   means for obtaining a magnitude spectrum of a complex spatial Fourier transform of a complex intermediate function, the complex intermediate function dependent on the complex scattering function of a portion of the sample, the magnitude spectrum obtained from power spectrum data of frequency-domain optical coherence tomography of the portion of the sample;
   means for estimating an estimated phase term of the complex spatial Fourier transform;
   means for multiplying the magnitude spectrum and the estimated phase term together to generate an estimated complex spatial Fourier transform;
   means for calculating an inverse Fourier transform of the estimated complex spatial Fourier transform, wherein the inverse Fourier transform of the estimated complex spatial Fourier transform is a spatial function; and
   means for calculating an estimated intermediate function by applying at least one constraint to the inverse Fourier transform of the estimated complex spatial Fourier transform.

14. The apparatus of claim 1, further comprising a general-purpose computer, the general-purpose computer comprising a non-transitory computer-readable medium having instructions stored thereon which cause the general-purpose computer to perform a method for determining the complex scattering function of a portion of the sample, the method comprising:
   (a) providing a magnitude spectrum of a complex spatial Fourier transform of a complex intermediate function, the complex intermediate function dependent on the complex scattering function of the portion of the sample, the magnitude spectrum obtained from power spectrum data of frequency-domain optical coherence tomography of the portion of the sample;
   (b) providing an estimated phase term of the complex spatial Fourier transform;
   (c) multiplying the magnitude spectrum and the estimated phase term together to generate an estimated complex spatial Fourier transform;
   (d) calculating an inverse Fourier transform of the estimated complex spatial Fourier transform, wherein the inverse Fourier transform of the estimated complex spatial Fourier transform is a spatial function; and
   (e) calculating an estimated intermediate function by applying at least one constraint to the inverse Fourier transform of the estimated complex spatial Fourier transform.

15. An apparatus for measuring a frequency-domain optical coherence tomography power spectrum from a sample, the apparatus configured to be optically coupled to a light source, the apparatus comprising:
   a partially reflective element optically coupled to the sample, the partially reflective element configured to reflect a first portion of light from the light source, the partially reflective element further configured to transmit a second portion of light in a first direction to impinge the sample and to transmit the second portion of light reflecting from the sample in a second direction opposite to the first direction, and
   an analyzer configured to receive the first and second portions of light and to measure the frequency-domain optical coherence tomography power spectrum in response to the first and second portions of light.

16. The apparatus of claim 15, further comprising an optical fiber optically coupled to the light source and the sample, the partially reflective element comprising an end of the optical fiber.

17. The apparatus of claim 16, wherein the end of the optical fiber is coated with a partially reflective material.

18. The apparatus of claim 15, wherein the apparatus further comprises a fiber coupler and a single optical fiber extending from the fiber coupler towards the sample.

19. The apparatus of claim 18, wherein the first portion of light and the second portion of light propagate along the single optical fiber extending from the fiber coupler towards the sample.

20. The apparatus of claim 19, wherein the analyzer uses the first portion of light as a reference signal.

* * * * *

UNITED STATES PATENT AND TRADEMARK OFFICE
CERTIFICATE OF CORRECTION

PATENT NO.       : 8,219,350 B2
APPLICATION NO.  : 13/224555
DATED            : July 10, 2012
INVENTOR(S)      : Ozcan et al.

It is certified that error appears in the above-identified patent and that said Letters Patent is hereby corrected as shown below:

In column 11, line 36, change " $R/\max\{|\eta(z')|\}$ ," to -- $R/\max\{f(z')\}$ --.

In column 11, line 55, change " $g(z')=R(z')+f(z'-z_0).$ " to -- $g(z') = R \cdot \delta(z') + f(z'-z_0) \cdot$ --.

In column 11, line 60, change " $\max\{|(z^1)|\} \geqq \sim 0.02.$ " to -- $\max\{f(z')\} \leq \sim 0.02 \cdot$ --.

Signed and Sealed this
Fourth Day of December, 2012

David J. Kappos
*Director of the United States Patent and Trademark Office*